(12) United States Patent
Mozo Grau

(10) Patent No.: US 10,517,700 B2
(45) Date of Patent: Dec. 31, 2019

(54) PROCEDURE FOR THE INDIVIDUAL TRACEABILITY OF DENTAL IMPLANTOLOGY PARTS AND A UNITARY IDENTIFICATION SYSTEM FOR IMPLEMENTING THIS PROCEDURE

(71) Applicant: FERMOINVERS, S.L., Valladolid (ES)

(72) Inventor: Fernando Mozo Grau, Valladolid (ES)

(73) Assignee: FERMOINVERS, S.L., Valladolid (ES)

( * ) Notice: Subject to any disclaimer, the term of this patent is extended or adjusted under 35 U.S.C. 154(b) by 299 days.

(21) Appl. No.: 15/526,065

(22) PCT Filed: Dec. 23, 2015

(86) PCT No.: PCT/ES2015/070944
§ 371 (c)(1),
(2) Date: May 11, 2017

(87) PCT Pub. No.: WO2016/107947
PCT Pub. Date: Jul. 7, 2016

(65) Prior Publication Data
US 2017/0325918 A1    Nov. 16, 2017

(30) Foreign Application Priority Data

Dec. 31, 2014  (ES) .................... 201431978

(51) Int. Cl.
*A61C 8/00*      (2006.01)
*G06K 19/06*     (2006.01)
(Continued)

(52) U.S. Cl.
CPC .............. *A61C 8/0093* (2013.01); *A61C 8/00* (2013.01); *G06K 19/06* (2013.01); *G06Q 10/08* (2013.01);
(Continued)

(58) Field of Classification Search
CPC ..... A61C 8/0093; A61C 8/00; A61C 2202/00; A61C 2204/005; G16B 50/00;
(Continued)

(56) References Cited

U.S. PATENT DOCUMENTS 6,290,500 B1 *  9/2001  Morgan .............. A61C 8/0048
                                                              433/173
9,839,496 B2 * 12/2017  Herrington ........ A61C 13/0004
(Continued)

FOREIGN PATENT DOCUMENTS

EP    2733631 A1    5/2014
ES    2324748 A1    8/2009
(Continued)

OTHER PUBLICATIONS

International Search Report, PCT/ES2015/070944, dated Jun. 4, 2016.
International Written Opinion, PCT/ES2015/070944 (translation).

*Primary Examiner* — Ashford S Hayles
(74) *Attorney, Agent, or Firm* — Hayes Soloway PC

(57) ABSTRACT

PROCEDURE FOR THE INDIVIDUAL TRACEABILITY OF DENTAL IMPLANT PARTS AND UNITARY IDENTIFICATION SYSTEM FOR IMPLEMENTING THIS PROCEDURE that comprises: the association of each part (1), which is manufactured with a single identification code (2); the incorporation of that code (2) into the individual packaging (3) in which the part (1) is distributed and marketed, recorded on a radio frequency label (5) and/or printed on an adhesive label (6); and the implementation of specific management software in a website (4) on the Internet that associated the code (2) with traceability information of each specific part (1), associates implants with accessories and provides a user with access to it in that website (4). The unitary identification system consists of a code (2) that is unique and different for each part (1), which
(Continued)

is a numerical code, and the specific management software that associates each code (2) with the traceability information of each part (1).

6 Claims, 1 Drawing Sheet

(51) Int. Cl.
*G06Q 10/08* (2012.01)
*G16B 50/00* (2019.01)
*G06Q 50/04* (2012.01)
G06K 19/07 (2006.01)
G06K 19/10 (2006.01)

(52) U.S. Cl.
CPC ........... *G06Q 10/087* (2013.01); *G06Q 50/04* (2013.01); *G16B 50/00* (2019.02); *A61C 2202/00* (2013.01); *A61C 2204/005* (2013.01); *G06K 19/06028* (2013.01); *G06K 19/0723* (2013.01); *G06K 19/10* (2013.01); *Y02P 90/30* (2015.11)

(58) Field of Classification Search
CPC ...... G06Q 10/087; G06Q 10/08; G06Q 50/04; G06K 19/06; G06K 19/06028; G06K 19/0723; G06K 19/10; Y02P 90/30
See application file for complete search history.

(56) References Cited

U.S. PATENT DOCUMENTS

| | | | |
|---|---|---|---|
| 2003/0139669 A1* | 7/2003 | Montegrande | A61B 5/06 600/426 |
| 2006/0134580 A1* | 6/2006 | Raby | A61C 13/16 433/213 |
| 2007/0006887 A1* | 1/2007 | Frank | A61F 2/38 128/899 |
| 2007/0050072 A1* | 3/2007 | Schwotzer | A61C 13/0022 700/116 |
| 2008/0108016 A1* | 5/2008 | Holzner | A61C 13/0003 433/203.1 |
| 2008/0200984 A1* | 8/2008 | Jodaitis | A61F 2/0095 623/17.16 |
| 2008/0230423 A1* | 9/2008 | Loeffler | A61B 17/865 206/438 |
| 2009/0266889 A1* | 10/2009 | Turner | A61L 2/07 235/385 |
| 2010/0096454 A1* | 4/2010 | Cloix | G06F 19/3418 235/385 |
| 2010/0274591 A1* | 10/2010 | Wells | G06Q 10/06 705/3 |
| 2010/0285429 A1* | 11/2010 | Karim | A61C 13/0022 433/199.1 |
| 2011/0208535 A1* | 8/2011 | Le Couedic | G06Q 50/22 705/2 |
| 2011/0229857 A1* | 9/2011 | Niewiadomski | A61C 13/0022 433/201.1 |
| 2013/0105577 A1* | 5/2013 | Hildreth | A61B 17/7001 235/385 |
| 2014/0095200 A1* | 4/2014 | Bostock | A61C 13/00 705/3 |
| 2014/0272790 A1* | 9/2014 | Aerni | A61C 8/0093 433/173 |
| 2015/0019252 A1* | 1/2015 | Dawson | A61C 8/00 705/3 |
| 2015/0149330 A1* | 5/2015 | Sweeney | G06Q 10/087 705/28 |
| 2015/0173843 A1* | 6/2015 | Maughan | A61B 17/80 705/3 |
| 2016/0042130 A1* | 2/2016 | Broninx | G06Q 10/087 705/2 |
| 2016/0249995 A1* | 9/2016 | Ritchey | A61B 17/865 53/425 |

FOREIGN PATENT DOCUMENTS

FR 2904211 A1 2/2008
WO 2013015552 A2 1/2013

* cited by examiner

PROCEDURE FOR THE INDIVIDUAL TRACEABILITY OF DENTAL IMPLANTOLOGY PARTS AND A UNITARY IDENTIFICATION SYSTEM FOR IMPLEMENTING THIS PROCEDURE

OBJECT OF THE INVENTION

As set out in the title of this descriptive report, the invention refers to a procedure for the individual traceability of dental implant parts and a unitary identification system to implement this procedure, thus contributing to the prior art a series of benefits and innovative characteristics that will be described in detail in the following pages, and entailing an important new development in its field.

In particular, the object of the invention is a procedure for implementing full, individual traceability of a specific dental implant and the prosthesis to be fitted to it, in order to allow any patient or dentist who wishes to do so to access the characteristics, specifications or technical manufacturing report of the implant whenever they need to. This procedure is based on the use of a unitary part identification system that operates by radio frequency, comprising a single code for each part and specific management software that enables such access via the Internet.

FIELD OF THE INVENTION

The field of the present invention is dentistry and in particular, the implant and implant prosthetics area.

BACKGROUND OF THE INVENTION

As in other fields, the law establishes the obligation to register the production of dental implants and their accessories by means of batch numbers that indicate the characteristics of the manufacturing and quality control processes and the starting materials used; this process is known as traceability. The grouping of these batches may be defined in accordance with different criteria, with the number of parts included being greater or smaller, depending on the chosen criteria, but in all cases, including a plurality of units.

All this information, along with the customer data (usually the dentists or dental clinics to which the parts of each batch are delivered) is recorded and stored in such a way that in the event of an incident, control can be exercised over each batch and, if necessary, the parts included in each batch can be recalled.

Although this traceability may provide certain information about the manufactured implant batches, it has limitations in relation to information on a particular implant. This could be relevant, for instance, in the hypothetical case that a dentist who is not the one responsible for the performing the implant procedure on the patient in the first place wishes to take an action with respect to the implant.

In addition, it should be said that each implant may have a wide range of different prostheses, depending on the needs of each case. As is known, prostheses or prosthetic accessories constitute the keystone or joining element between the implant, which is the metal part inserted into the bone, and the crown, which is the external part. That large variety leads to multiple possibilities in combining the different implants and prostheses placed in each patient.

The object of this invention is therefore to develop a traceability procedure that goes one step further than tracing batches, and is focused on each of the parts manufactured individually. In particular, it permits the option of monitoring the individual traceability of each part from the time it is manufactured for the end patient, to the moment the implant is put in place, by any dentist who may, for any reason, need to take action on that specific implant, in order to access that information at any time, and from any place.

On the other hand, in reference to the prior art, it should be said that although different systems and methods exist for the traceability and identification of products, the applicant, at least, is not aware of the existence of any procedure or invention that disseminates or describes the present procedure that is claimed here.

EXPLANATION OF THE INVENTION

Thus, the individual traceability procedure and unitary identification system for implants and prostheses proposed by this invention is configured as an important novelty in its field, as the objectives considered ideal that are set out above are satisfactorily achieved, based on its implementation, and in an exhaustive manner, with the characterising details that make this possible correctly included in the final claims attached to the present description.

In particular, what the invention proposes, as stated earlier, is firstly a procedure to ensure the traceability of a dental implant and the prosthesis connected to it, providing complete and individual information on that implant and prosthesis in particular, from the precise moment of their fabrication, and thus permitting any patient or dentist to know the characteristics, specification or technical information regarding the production of that part, and secondly, a unitary identification system to perform that individual traceability, based on the use of a numerical code and management software.

More specifically, the traceability procedure comprises the use of a single numerical code linked with the part, which is unique and different for each part.

This numerical code is the unitary means for identifying each part, and is used to access information on the fabrication of the part to be offered by means of management software. Thus, when the numerical code is entered in the specific section of a website posted for that purpose through an Internet server that uses the above management software, this gives access to a file containing the foregoing information on the part associated with that numerical code.

In turn, each part, regardless of whether it is an implant or a prosthesis, is associated with a single numerical code at the time of its fabrication. That numerical code is recorded on a RFID (Radio Frequency IDentification) radio frequency label that is incorporated into the packaging, preferably a blister type pack, in which the parts are distributed and marketed, or recorded on a bar code.

In addition, the numerical code is also printed in figures on the respective adhesive labels attached to the packaging of the part, so that one of these labels can be filed by the dentist who acquires the implant or prosthesis and performs the placement procedure on the patients and the other can be kept by the patients themselves.

Thus, through the management software, the health professional performing the implant will be able to link the prosthesis code with the implant placed in each patient, as each implant has a prosthesis or accessory connected to it. So normally, each patient will have a label with the numerical code of their implant, and through the software, the code of the prosthetic accessory placed in the patient will have been linked to that numerical code, thus allowing them to access the information on the fabrication of both parts via the above-mentioned website. This can be done at any time and from any place through any device allowing Internet access.

In this way, the procedure allows the patients to know the exact characteristics of their implant and prosthesis or prosthetic accessory, the technical drawing, material, date of manufacture and verification date and even the persons intervening in each of the manufacturing processes, the part verification and the respective reference and batch numbers, and all other information that is to be provided.

Through the website the patient, doctor or dentist who needs to obtain information on the implant and the prosthesis will enter the numerical code of the implant in the respective section and be able to access the data enabling them to know the technical characteristics of the implant and the accessory; for instance, the type of screw, material or other information with respect to the patient's implant. The data will also be useful in furnishing additional information on the connection or prosthetic accessory implanted, such as the thread pitch of the implant, the size of the accessory connected to the implant or the personalised prosthesis manufactured for the patient's dental space, without the need to access or disassemble the crown or the implant.

Thus, for example, given the ease with which a person can now travel to any part of the world, in the event of suffering a problem with their prosthesis, a patient can pay a visit to a dentist who will be able to quickly and easily obtain information on the implant placed in the patient such as the type of implant, the connection, the thread pitch, the prosthetic accessory, etc., and therefore solve the problem using the appropriate tools.

In the light of the above, it is stated that the described procedure for the individual traceability of dental implants and the unitary identification system for implementing that traceability are innovations with structural and constituent characteristics hitherto unknown for the purpose for which they are intended, and these reasons, together with their practical and useful nature, are sufficient grounds to allow them to obtain the privilege of exclusivity that is being sought.

DESCRIPTION OF THE DRAWINGS

To complete the description, and with a view to helping to obtain a better understanding of the characteristics of the invention, a set of drawings is attached to this descriptive report, forming an inseparable part hereof, showing the following, as examples and without limitation.

PREFERENTIAL IMPLEMENTATION OF THE INVENTION

Figure 1:
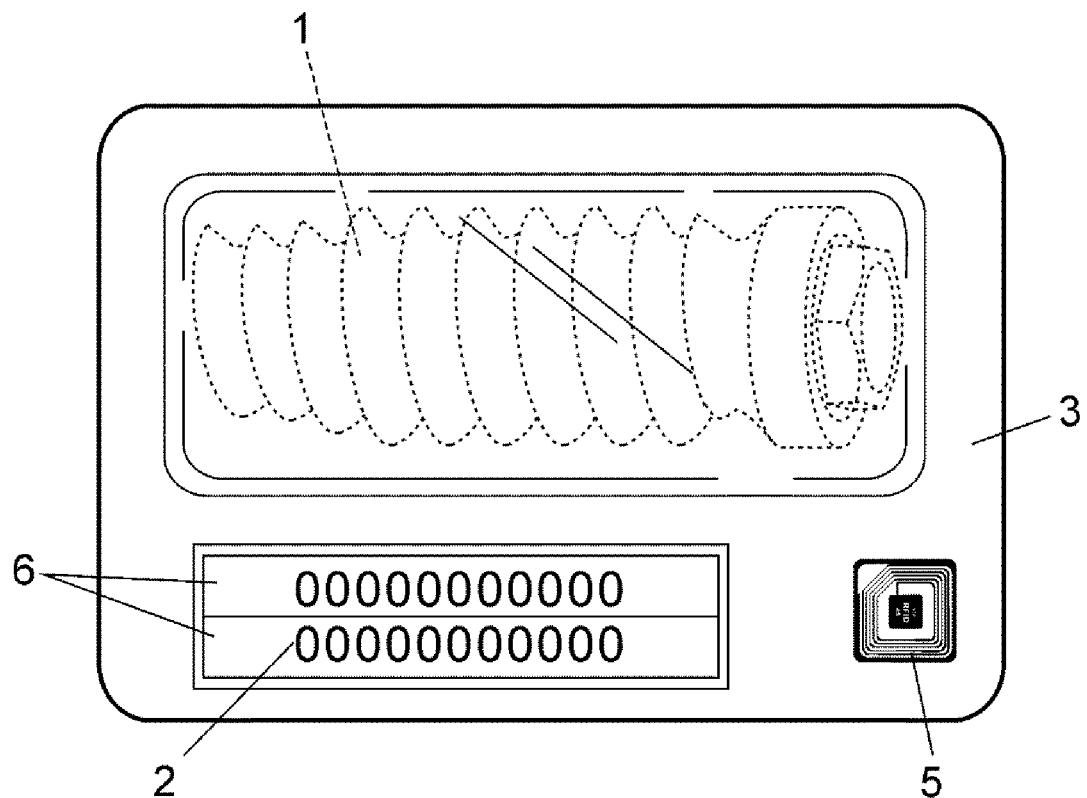
FIG. 1.—This shows a diagrammatic view of an example of a dental implant inside its commercial packaging, in which the labels are included with the numerical code associated with that implant, constituting the unitary identification method for the same, in order to access its traceability.
Figure 2:
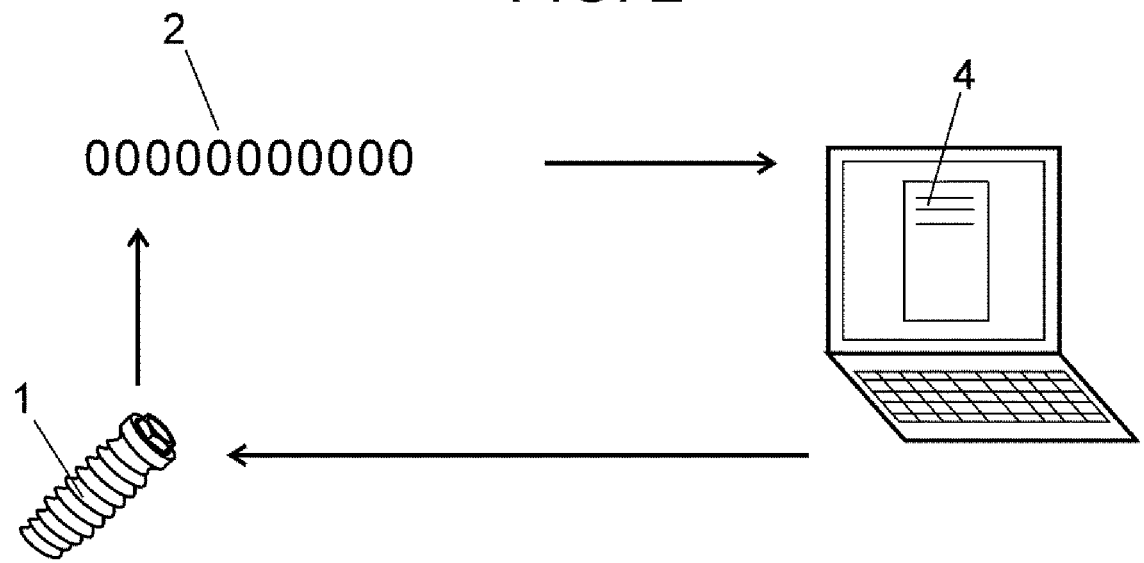
FIG. 2.—This gives a schematic description of the traceability procedure, in accordance with the invention.

FIG. 1 shows an example of a dental implant part (1), specifically, an implant, although it must be considered that it could also be a prosthesis or a prosthetic accessory, inside the individual blister type packaging (3) in which it is distributed and marketed, in which the innovative element is the single identification code (2) that is unique to that part, for accessing its traceability.

In particular, the code (2), which will preferably be a numerical code with multiple digits, is included on that packaging (3), recorded on a radio frequency label (5) or a bar code and printed in figures on two adhesive labels (6). Logically, the code (2) may be recorded on a radio frequency label (5) and more or fewer copies can be made of it, and/or on more or fewer bar codes, and/or printed on more or fewer adhesive labels (6), as is convenient or considered necessary.

At all events, the numerical, single code (2) that is unique for each part (1), together with specific management software that associates/links each code (2) with the traceability information and specific fabrication characteristics of each part (1) with which the code is associated (2) make up the unitary identification system that will permit the individual traceability of the parts (1), in accordance with the described procedure, for which purpose the management software is implemented on a website (4) which, thanks to the respective server, is accessible via the Internet and allows a user to gain access to the traceability information by entering in it the code (2) of a specific part (1), in other words, to the specific fabrication characteristics of each specific part (1).

In summary, the traceability procedure comprises:
association of the parts (1), after completion of the manufacturing process, with the identification code (2), which is unique and different for each part (1);
incorporation into the individual packaging (3) in which each part (1) is distributed and marketed of the unique identification code (2) associated with it;
and the implementation of specific management software linking the parts in the website (4) on the Internet, which associates the single identification code (2) of each part (1) with the traceability information and specific fabrication characteristics of that particular part (1), associating the identification code (2) of a part (1) consisting of an implant with the identification code of another part (1) consisting of an accessory or a prosthesis, storing all the traceability information of both parts (for the health professional performing the implant procedure to associate the code (2) of the accessory with the code of the implant that he places in each patient), and also providing access to that information when the code (2) of the implant part (1) is entered in that website (4) by a user.

In turn, the unitary identification system that allows this procedure to be carried out is made up of the identification code (2), which is a single numerical code that is different for each part (1), and the specific management software that associates/links each code (2) with the traceability information and the specific fabrication characteristics of each particular part (1) with which that code (2) is associated, and the identification code (2) to be linked to an implant part (1) identifying an accessory or a prosthetic part (1).

Having described in sufficient detail the nature of this invention and the manner in which it is put into practice, it is not considered necessary to go into any further detail to allow an expert in the matter to understand its scope and the benefits it brings. It is stated that, within its essential design, it may be put into practice using other methods of implementation that differ in detail from that indicated as an example, which will also enjoy the protection sought, provided the fundamental principle is not altered, changed or modified.

The invention claimed is:
1. PROCEDURE FOR THE INDIVIDUAL TRACEABILITY OF DENTAL IMPLANT PARTS, in particular, first parts that constitute dental implants and second parts that constitute the prostheses to be connected to an implant, wherein the procedure includes the following steps:

association of first parts and second parts, once a fabrication process has concluded, with an identification code that is unique and different for each first part of the first parts and for each second part of the second parts;

incorporation into a first individual packaging in which each first part is distributed and marked with the unique identification code associated with each first part;

incorporation into a second individual packaging in which each second part is distributed and marked with the unique identification code associated with each second part;

implementation of specific management software linking the first parts and the second parts in a website on the Internet, which associates the single identification code of each first part and each second part with the traceability information and specific fabrication characteristics of that first part or second part, respectively, in particular, which associates the identification code of a first part with the identification code of a second part, storing all the traceability information of both first part and second part and giving access to that information, when the code of that first part or second part is entered in the website by a user.

2. PROCEDURE FOR THE INDIVIDUAL TRACEABILITY OF DENTAL IMPLANT PARTS based on claim 1, wherein the single identification code is a numerical code.

3. PROCEDURE FOR THE INDIVIDUAL TRACEABILITY OF DENTAL IMPLANT PARTS as set out in claim 1 wherein a single identification code is incorporated into the first individual packaging of each first part and into the second individual packaging of each second part, or at least recorded on a radio frequency label.

4. PROCEDURE FOR THE INDIVIDUAL TRACEABILITY OF DENTAL IMPLANT PARTS, of claim 1, wherein a single identification code is incorporated into the first individual packaging of each first part and into the second individual packaging of each second part, or at least printed on an adhesive label.

5. PROCEDURE FOR THE INDIVIDUAL TRACEABILITY OF DENTAL IMPLANT PARTS, of claim 1, wherein the single identification code is incorporated into the first individual packaging of each first part and into the second individual packaging of each second part recorded on a radio frequency label and printed on two adhesive labels.

6. UNITARY IDENTIFICATION SYSTEM for the implementation of an individual traceability procedure for implant parts, in particular, first parts that constitute dental implants and second parts that constitute the prostheses to be connected to an implant, wherein the system consists of a numerical code that is unique and different for each first part and each second part, and specific management software that associates each code with the traceability information and specific fabrication characteristics of each part with which each code is associated, and that associates/links the identification code of a first part with the identification code of the second part.

\* \* \* \* \*